United States Patent
Taguchi (10) Patent No.: US 11,195,108 B2
(45) Date of Patent: Dec. 7, 2021

(54) ABNORMALITY DETECTION DEVICE AND ABNORMALITY DETECTION METHOD FOR A USER

(71) Applicant: Mitsubishi Electric Corporation, Tokyo (JP)

(72) Inventor: Shinya Taguchi, Tokyo (JP)

(73) Assignee: MITSUBISHI ELECTRIC CORPORATION, Tokyo (JP)

(*) Notice: Subject to any disclaimer, the term of this patent is extended or adjusted under 35 U.S.C. 154(b) by 24 days.

(21) Appl. No.: 16/842,462

(22) Filed: Apr. 7, 2020

(65) Prior Publication Data

US 2020/0234161 A1     Jul. 23, 2020

Related U.S. Application Data (63) Continuation of application No. PCT/JP2017/041861, filed on Nov. 21, 2017.

(51) Int. Cl.
*G08B 21/00* (2006.01)
*G06N 5/04* (2006.01)
(Continued)

(52) U.S. Cl.
CPC ............. *G06N 5/04* (2013.01); *A61B 5/1116* (2013.01); *A61B 5/18* (2013.01); *A61B 5/7267* (2013.01); *G06N 20/00* (2019.01)

(58) Field of Classification Search
CPC ........ G06N 5/04; G06N 20/00; A61B 5/1116; A61B 5/18; A61B 5/7267; A61B 5/021; A61B 5/024; A61B 5/6893; G08G 1/16
(Continued)

(56) References Cited

U.S. PATENT DOCUMENTS 10,067,505 B2    9/2018  Ichikawa et al.
10,445,603 B1 * 10/2019  Quach ................ G06K 9/00832
(Continued)

FOREIGN PATENT DOCUMENTS

DE    10 2016 212 422 A1    1/2017
JP         2016-9255 A       1/2016

OTHER PUBLICATIONS

German Office Action issued in corresponding German Patent Application No. 112017008148.3 dated Feb. 19, 2021 with an English Translation.
(Continued)

*Primary Examiner* — Mark S Rushing
(74) *Attorney, Agent, or Firm* — Birch, Stewart, Kolasch & Birch, LLP (57) ABSTRACT

An abnormality detection device acquires sensor information indicating a state of a person and device information indicating a state of a device, determines whether there is a combination corresponding to the acquired sensor information and acquired device information in a learning database, and determines whether there is sensor information or device information corresponding to the acquired sensor information or the acquired device information in a behavior pattern database. If it is determined that the acquired sensor information is not in a normal range, the device determines that a current state is in the normal state when it is determined that there is the corresponding combination, and determines that the current state is in an abnormal state when it is determined that there is no corresponding combination and no corresponding sensor information or device information.

5 Claims, 5 Drawing Sheets

(51) Int. Cl.
*G06N 20/00* (2019.01)
*A61B 5/11* (2006.01)
*A61B 5/18* (2006.01)
*A61B 5/00* (2006.01)

(58) Field of Classification Search
USPC .......................................................... 340/576
See application file for complete search history.

(56) References Cited

U.S. PATENT DOCUMENTS

| 10,457,165 | B2 * | 10/2019 | Toyoda | B60W 40/08 |
| 2011/0169625 | A1 * | 7/2011 | James | G08G 1/166 |
| | | | | 340/439 |
| 2015/0254955 | A1 * | 9/2015 | Fields | G08B 21/02 |
| | | | | 705/4 |
| 2017/0161575 | A1 * | 6/2017 | Banno | G06K 9/00228 |
| 2020/0082190 | A1 | 3/2020 | Banno et al. | |

OTHER PUBLICATIONS

Mittal et al., "Head movement-based driver drowsiness detection: A review of state-of-art techniques", $2^{nd}$ IEEE International Conference on Engineering and Technology (ICETECH), Mar. 17-18, 2016, pp. 1-6.

Takahashi et al., "Automated safety vehicle stop system for cardiac emergencies", 2016 IEEE International Conference on Emerging Technologies and Innovative Business Practices for the Transformation of Societies (EmergiTech), (2016), total of 4 pages.

* cited by examiner

|   | Sensor Information | Device Information |
|---|---|---|
|   |   |   |

FIG. 5B

|   | Sensor Information | Device Information |
|---|---|---|
| 1 | ● Face Position A (High-Density Distribution) |   |

FIG. 5C

|   | Sensor Information | Device Information |
|---|---|---|
| 1 | ● Face Position A (High-Density Distribution) | None |
| 2 | ▲ Face Position B (Low-Density Distribution) | High Brake Frequency And Steering To Right |
| 3 | ○ Face Position C (Low-Density Distribution) | High Brake Frequency And Steering To Left |

FIG. 6

| 1 | It Is Indicated That Eyes Are Open For Period Of Time Equal To Or Longer Than First Set Time |
| --- | --- |
| 2 | It Is Indicated That Music Has Been Selected In Car Navigation Device |
| 3 | It Is Indicated That Temperature Of Car Air Conditioner Has Been Set |
| | ... |

ABNORMALITY DETECTION DEVICE AND ABNORMALITY DETECTION METHOD FOR A USER

CROSS REFERENCE TO RELATED APPLICATION

This application is a Continuation of PCT International Application No. PCT/JP2017/041861, filed on Nov. 21, 2017, which is hereby expressly incorporated by reference into the present application.

TECHNICAL FIELD

The present invention relates to an abnormality detection device that detects the occurrence of an abnormal state.

BACKGROUND ART

Devices are known which detect the occurrence of an abnormal state and sound an alarm or the like. Such a device is configured to detect that an abnormal state has occurred when a person suddenly loses consciousness or a suspicious person enters. A specific example of such a device is a driver monitoring system (hereinafter referred to as a "DMS"). The DMS senses a state of a driver in order to prevent a traffic accident caused by poor health or the like of the driver, and has been developed rapidly in recent years. Regarding the DMS, expectation is growing for functions of detecting the occurrence of an abnormal state such as a case where a driver becomes unconscious due to sudden illness, falling asleep, or the like, and is thus unable to drive, and outputting a warning or performing a safe stop in automatic driving, and the like.

For example, Patent Literature 1 describes a driving incapability state detector that detects a driver's driving incapability state by using a seat belt sensor that detects the amount of seat belt drawn, a seat surface sensor that detects pressure distribution in a driver's seat, and a driver camera that captures the driver's seat. The driving incapability state detector of Patent Literature 1 detects the driving incapability state on the basis of a position of the head of the driver. In addition, when the driving incapability state detector of Patent Literature 1 erroneously detects that the driver is in the driving incapability state, the driving incapability state detector learns a posture of the driver at that time. Then, regarding the learned posture, the driving incapability state detector of Patent Literature 1 does not determine that it is the driving incapability state.

CITATION LIST

Patent Literatures

Patent Literature 1: JP 2016-9255 A

SUMMARY OF INVENTION

Technical Problem

In an abnormality detection device that detects the occurrence of an abnormal state, it is required to accurately discriminate between abnormal and normal states.

Since the driving incapability state detector of Patent Literature 1 learns a posture of the driver at the time of erroneous detection, a posture of the driver when driving, such as a posture of leaning forward and peering through the windshield or resting his/her chin on his/her hand, is learned as a normal state. However, the posture of the driver when driving, such as the posture of leaning forward and peering through the windshield or resting his/her chin on his/her hand, is similar to a posture when the driver collapses due to loss of consciousness or the like, which is confusing. Therefore, even when the driver really collapses due to loss of consciousness or the like, the driving incapability state detector of Patent Literature 1 determines that it is a normal state since the posture has been learned.

As described above, the conventional device that regards the learned posture as a normal state has a low accuracy of discrimination between abnormal and normal states.

The present invention has been made in order to solve the above-described problem, and an object thereof is to provide an abnormality detection device capable of improving the accuracy of discrimination between abnormal and normal states.

Solution to Problem

An abnormality detection device according to the present invention includes: processing circuitry to acquire sensor information indicating a state of a person and device information indicating a state of a device; to determine whether the acquired sensor information is in a normal range; to determine whether there is a combination corresponding to a combination of the acquired sensor information and the acquired device information in a learning database in which one or more combinations of the sensor information and the device information in a normal state are stored; to determine whether there is sensor information or device information corresponding to the acquired sensor information or the acquired device information in a behavior pattern database in which the sensor information or the device information in the normal state is stored; in a case where it is determined that the acquired sensor information is not in the normal range, to determine that a current state is in the normal state when it is determined that there is the corresponding combination, and to determine that the current state is in an abnormal state when it is determined that there is no corresponding combination and no corresponding sensor information or device information; and in the case where it is determined that the acquired sensor information is not in the normal range, to register the combination of the acquired sensor information and the acquired device information in the learning database when it is determined that there is no corresponding combination, and it is determined that there is the corresponding sensor information or device information.

Advantageous Effects of Invention

According to the present invention, a combination of the sensor information and the device information acquired is registered in the learning database depending on the three types of determination, and is used for discriminating the abnormal state. Therefore, the accuracy of discrimination between abnormal and normal states is improved.

BRIEF DESCRIPTION OF DRAWINGS

FIG. 5C is a table illustrating an example of the learning database when FIG. 5B is updated.

DESCRIPTION OF EMBODIMENTS

Hereinafter, in order to describe the present invention in more detail, an embodiment of the present invention will be described with reference to the attached drawings.

First Embodiment

Figure 1:
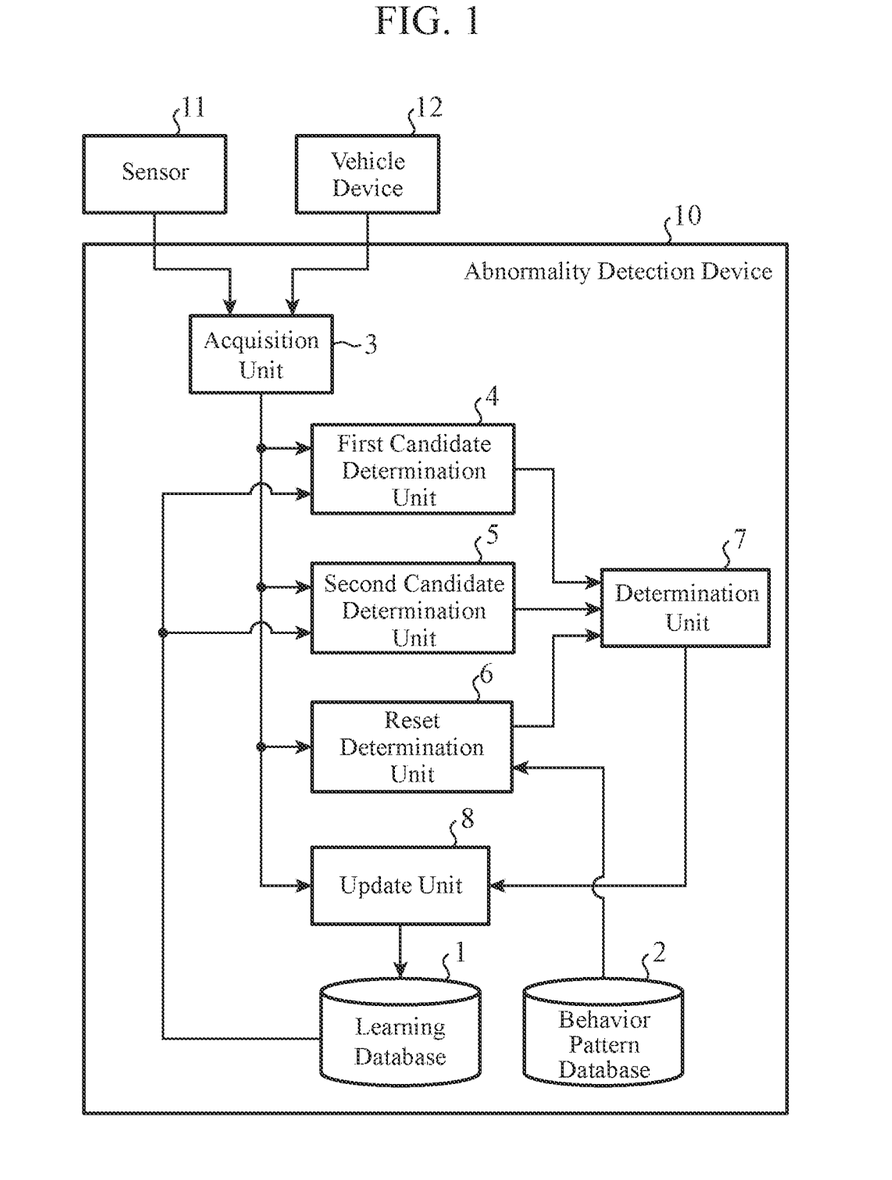
FIG. 1 is a diagram illustrating a configuration of an abnormality detection device according to a first embodiment.

FIG. 1 is a diagram illustrating a configuration of an abnormality detection device 10 according to a first embodiment. In the first embodiment, the abnormality detection device 10 will be described assuming that the abnormality detection device 10 is mounted on a vehicle and detects an abnormal state of a driver of the vehicle.

The abnormality detection device 10 includes a learning database 1, a behavior pattern database 2, an acquisition unit 3, a first candidate determination unit 4, a second candidate determination unit 5, a reset determination unit 6, a determination unit 7, and an update unit 8. The abnormality detection device 10 is connected to a sensor 11 and a vehicle device 12.

The sensor 11 generates sensor information indicating a state of the driver of the vehicle and outputs the sensor information to the abnormality detection device 10. For example, the sensor 11 detects a position of the driver's face or positions of the driver's eyes, and outputs sensor information indicating the position of the driver's face or the positions of the driver's eyes to the abnormality detection device 10. In that case, the sensor 11 includes, for example, a visible camera or an infrared camera installed in the vehicle, and an image analysis device that analyzes captured images obtained by these cameras. A plurality of cameras may be installed in the vehicle as cameras included in the sensor 11. The sensor 11 may include, in addition to the camera and the image analysis device, a microphone and a voice recognition device installed in the vehicle, and the voice of an occupant such as a driver may be recognized and included in the sensor information.

The sensor 11 may be a biological sensor that generates sensor information indicating a driver's heart rate, blood pressure, or the like, or may be a pressure-sensitive sensor installed in a driver's seat.

The vehicle device 12 generates device information indicating a state of the device and outputs the device information to the abnormality detection device 10. The vehicle device 12 is, for example, a steering wheel, an accelerator, a brake, a gear, a car air conditioner, a car navigation device, a speedometer, an accelerometer, a thermometer, a hygrometer, or a global positioning system (GPS) device. The vehicle device 12 outputs, as device information, operation information on the steering wheel, the accelerator, the brake, or the gear, operation information on the car air conditioner or the car navigation device, or information on the vehicle itself such as vehicle speed, temperature, humidity, or a travel trajectory.

The sensor information output by the sensor 11 and the device information output by the vehicle device 12 are acquired by the acquisition unit 3 of the abnormality detection device 10. The acquisition unit 3 outputs the acquired sensor information and device information to the first candidate determination unit 4, the second candidate determination unit 5, the reset determination unit 6, and the update unit 8.

The learning database 1 stores combinations of sensor information and device information in a normal state. In the learning database 1, each of the combinations of sensor information and device information may be stored together with time when the combination is stored in the learning database 1. When the abnormality detection device 10 is mounted on a vehicle as in the first embodiment, the normal state specifically means that the driver is not in a state of sudden illness or dozing, but in a state where normal driving is possible.

The behavior pattern database 2 stores sensor information or device information in the normal state. The sensor information or the device information stored in the behavior pattern database 2 is information that clearly illustrates that it is the normal state, and is information that satisfies one of the following conditions, for example. In other words, it can be said that behavior patterns that are generally considered to be those in the normal state are stored in the behavior pattern database 2.

It is indicated that eyes are open for a period of time equal to or longer than a first set time.

It is indicated that parking in reverse has been completed.

It is indicated that music has been selected in a car navigation device.

It is indicated that a temperature of a car air conditioner has been set.

It is indicated that a driver and a person in the passenger seat have had a conversation with smiles.

A travel trajectory at a time of completing a right or left turn is indicated.

In the behavior pattern database 2, the sensor information or the device information that satisfies any of the above conditions is registered in advance, for example, at a time of product shipment. Alternatively, a user of the abnormality detection device 10 may manually set the behavior pattern database 2 when using the abnormality detection device 10.

The first candidate determination unit 4 determines whether the sensor information acquired by the acquisition unit 3 is in a normal range. For example, when the sensor information acquired by the acquisition unit 3 indicates the position of the driver's face, the first candidate determination unit 4 determines how far the position of the driver's face deviates from the position of the driver's face during normal driving. Then, when there is a deviation equal to or larger than a first set value, the first candidate determination unit 4 determines that the sensor information acquired by the acquisition unit 3 is not in the normal range, and when the deviation is less than the first set value, the first candidate determination unit 4 determines that the sensor information acquired by the acquisition unit 3 is in the normal range.

The first candidate determination unit 4 outputs a result of the determination to the determination unit 7.

The second candidate determination unit 5 determines whether there is a combination corresponding to the combination of the sensor information and the device information acquired by the acquisition unit 3, among the combinations of the sensor information and the device information stored in the learning database 1. Details will be described later. What is meant by being "corresponding" is not limited to being strictly corresponding, and when combinations are similar to each other enough to be regarded as substantially corresponding, the combinations may be determined to be corresponding to each other. The same applies to determination by the reset determination unit 6.

The second candidate determination unit 5 outputs a result of the determination to the determination unit 7.

The reset determination unit 6 determines whether there is sensor information or device information corresponding to the sensor information or the device information acquired by the acquisition unit 3, in the sensor information or the device information stored in the behavior pattern database 2.

The reset determination unit 6 outputs a result of the determination to the determination unit 7.

The determination unit 7 determines that it is the normal state or that it is the abnormal state depending on the determination results by the first candidate determination unit 4, the second candidate determination unit 5, and the reset determination unit 6.

The update unit 8 receives an instruction from the determination unit 7 depending on the determination results by the first candidate determination unit 4, the second candidate determination unit 5, and the reset determination unit 6, and registers the combination of the sensor information and the device information acquired by the acquisition unit 3 in the learning database 1. In this way, the combination of the sensor information and the device information learned by the abnormality detection device 10 as a combination of sensor information and device information in the normal state is registered in the learning database 1.

Next, example hardware configurations of the abnormality detection device 10 will be described with reference to FIGS. 2A and 2B.

The acquisition unit 3, the first candidate determination unit 4, the second candidate determination unit 5, the reset determination unit 6, the determination unit 7, and the update unit 8 of the abnormality detection device 10 are implemented by a processing circuit. In other words, the abnormality detection device 10 includes a processing circuit for detecting the occurrence of an abnormal state by acquiring the sensor information and the device information. The processing circuit may be dedicated hardware as illustrated in FIG. 2A, or may be a central processing unit (CPU) that executes a program stored in a memory as illustrated in FIG. 2B. The CPU is also called a central processing device, a processing device, an arithmetic device, a microprocessor, a microcomputer, a processor, or a digital signal processor (DSP).

The learning database 1 and the behavior pattern database 2 are implemented using a hard disk drive (HDD) 104. Note that there is no limitation to the HDD, and the learning database 1 and the behavior pattern database 2 may be implemented using a digital versatile disc (DVD) or the like similarly to a memory 102 described later.

The abnormality detection device 10 further includes an input interface device 105 and an output interface device 106 for performing communication with an external device or external software.

Figure 2A:
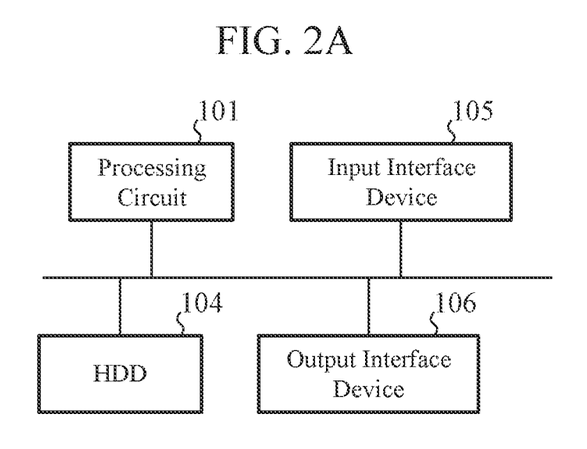
FIG. 2A and FIG. 2B are diagrams each illustrating an example hardware configuration of the abnormality detection device according to the first embodiment.

FIG. 2A illustrates an example hardware configuration when the functions of the acquisition unit 3, the first candidate determination unit 4, the second candidate determination unit 5, the reset determination unit 6, the determination unit 7, and the update unit 8 are implemented by a processing circuit 101 that is dedicated hardware. The processing circuit 101 corresponds to, for example, a single circuit, a composite circuit, a programmed processor, a parallel programmed processor, an application specific integrated circuit (ASIC), a field programmable gate array (FPGA), or a combination thereof. The functions of the acquisition unit 3, the first candidate determination unit 4, the second candidate determination unit 5, the reset determination unit 6, the determination unit 7, and the update unit 8 may be implemented by combining two or more processing circuits 101, or may be implemented by one processing circuit 101.

Figure 2B:
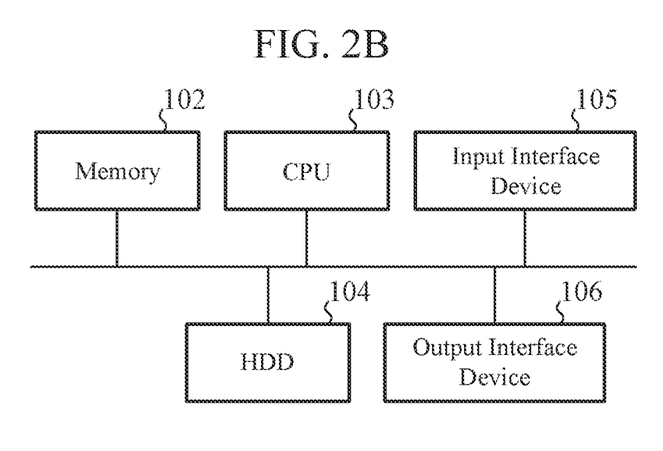

FIG. 2B is a diagram illustrating an example hardware configuration when the functions of the acquisition unit 3, the first candidate determination unit 4, the second candidate determination unit 5, the reset determination unit 6, the determination unit 7, and the update unit 8 are implemented by a CPU 103 executing programs stored in the memory 102. In that case, the functions of the acquisition unit 3, the first candidate determination unit 4, the second candidate determination unit 5, the reset determination unit 6, the determination unit 7, and the update unit 8 are implemented by software, firmware, or a combination of software and firmware. The software and the firmware are each described as a program and stored in the memory 102. The CPU 103 implements the functions of the acquisition unit 3, the first candidate determination unit 4, the second candidate determination unit 5, the reset determination unit 6, the determination unit 7, and the update unit 8 by reading and executing programs stored in the memory 102. More specifically, the abnormality detection device 10 includes the memory 102 for storing programs and the likes with which Steps ST1 to ST8 illustrated in the flowchart of FIG. 3 to be described later are executed as a result. In addition, it can also be said that these programs cause a computer to execute procedures or methods of the acquisition unit 3, the first candidate determination unit 4, the second candidate determination unit 5, the reset determination unit 6, the determination unit 7, and the update unit 8. The CPU 103 may include a plurality of cache memories such as a primary cache memory and a secondary cache memory. Here, the memory 102 corresponds to, for example, a non-volatile or volatile semiconductor memory such as a random access memory (RAM), a read only memory (ROM), a flash memory, an erasable programmable ROM (EPROM), or an electrically erasable programmable ROM (EEPROM), or a disk-shaped recording medium such as a magnetic disk, a flexible disk, an optical disk, a compact disc, a mini disk, or a DVD.

Regarding the functions of the acquisition unit 3, the first candidate determination unit 4, the second candidate determination unit 5, the reset determination unit 6, the determination unit 7, and the update unit 8, a part thereof may be implemented by dedicated hardware, and another part thereof may be implemented by software or firmware. For example, the function of the acquisition unit 3 can be implemented by a processing circuit as dedicated hardware, and the functions of the first candidate determination unit 4, the second candidate determination unit 5, the reset determination unit 6, the determination unit 7, and the update unit 8 can be implemented by a processing circuit reading and executing programs stored in a memory.

As described above, the processing circuit can implement the functions of the acquisition unit 3, the first candidate determination unit 4, the second candidate determination unit 5, the reset determination unit 6, the determination unit 7, and the update unit 8 by using hardware, software, firmware, or a combination thereof.

Next, an example of a process performed by the abnormality detection device 10 configured as described above will be described with reference to the flowchart illustrated in FIG. 3. Hereinafter, as an example, a case will be described where the sensor 11 includes a camera and outputs sensor information indicating a position of a driver's face as a state of a person.

Figure 3:
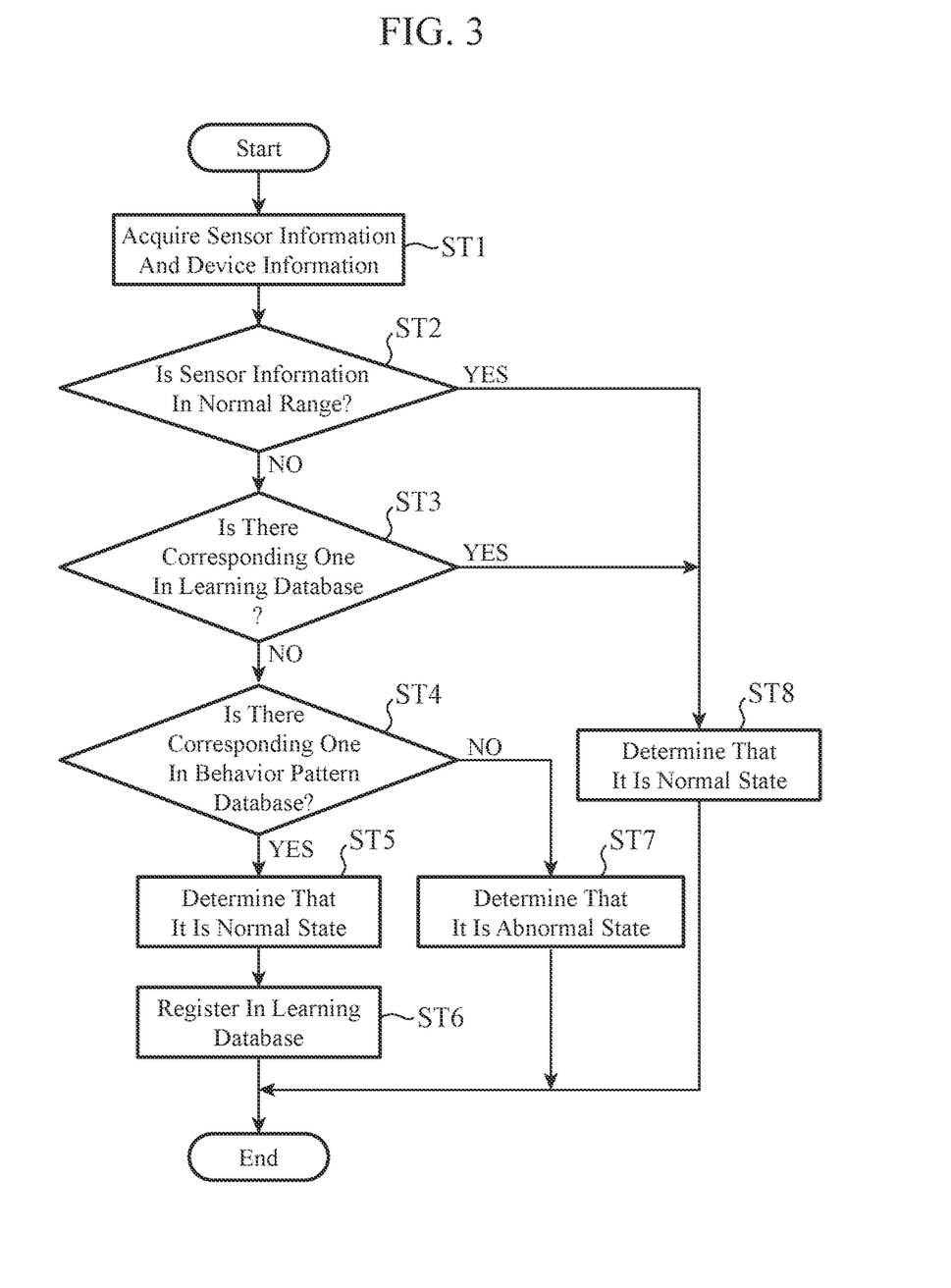
FIG. 3 is a flowchart illustrating an example of a process performed by the abnormality detection device according to the first embodiment.

The process illustrated in the flowchart of FIG. 3 is periodically performed after a vehicle engine is turned on, for example.

In the following, a "normal state data collection phase" including a registration process in the learning database 1 will be described first as a process flow, and subsequently an "abnormality detection phase" that does not lead to the registration process in the learning database 1 will be described as a process flow.

The acquisition unit 3 acquires sensor information from the sensor 11 and acquires device information from the vehicle device 12 (Step ST1). The acquisition unit 3 outputs the acquired sensor information and device information to the first candidate determination unit 4, the second candidate determination unit 5, the reset determination unit 6, and the update unit 8.

Figure 4A:
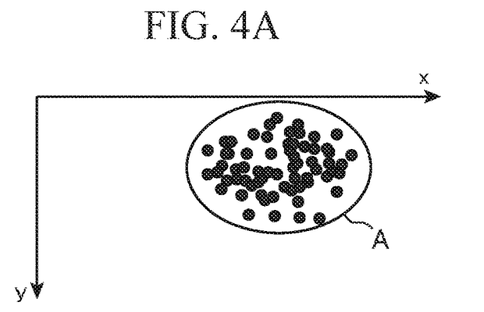
FIG. 4A is a diagram illustrating an example of a position of a driver's face that is in a normal range.
Figure 5A:
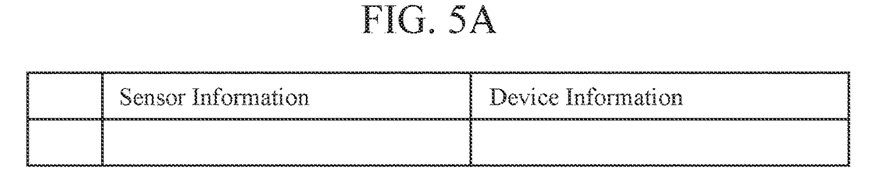
FIG. 5A is a table illustrating an example of a learning database at the start of traveling.
Figure 5B:
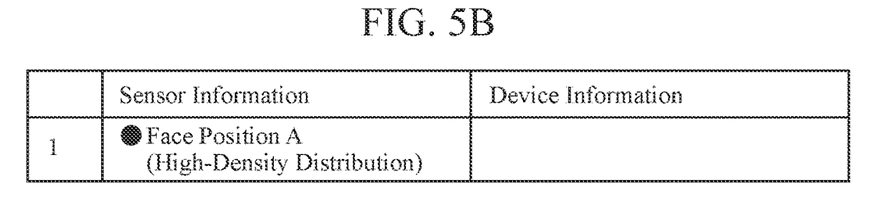
FIG. 5B is a table illustrating an example of the learning database one minute after the start of traveling.

The acquisition unit 3 also performs a process of registering, in the learning database 1, the sensor information acquired during a certain period, for example, one minute after the vehicle engine is turned on and the vehicle starts traveling, assuming that it is a normal state during the certain period. For example, it is assumed that sensor information indicating a high-density face position distribution A as illustrated in FIG. 4A is obtained within one minute from the start of traveling. In that case, the learning database 1 at the start of traveling is that illustrated in FIG. 5A as an example, but will be that illustrated in FIG. 5B as an example after the elapse of one minute from the start of traveling. The sensor information registered in this way indicates the normal range of the sensor information. Instead of the registration by the acquisition unit 3, sensor information indicating a position of a driver's face, the position being generally considered to be normal, may be registered in advance in the learning database 1 by default, for example, at the time of product shipment.

Subsequently, the first candidate determination unit 4 determines whether the sensor information acquired by the acquisition unit 3 is in the normal range (Step ST2). The first candidate determination unit 4 outputs a result of the determination to the determination unit 7.

Figure 4B:
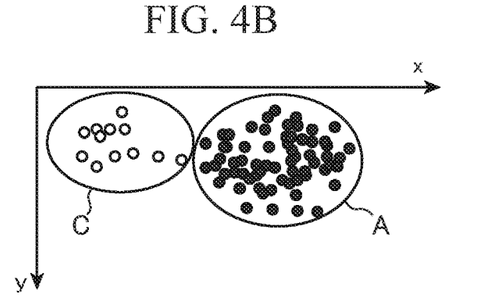
FIG. 4B is a diagram illustrating examples of the position of the driver's face that is in the normal range and a position of the face of the driver who is leaning forward.

For example, when the driver is bending over as a result of leaning forward and peering through the windshield while driving, or the like, and thereby the position of the driver's face moves, a face position distribution C as illustrated in FIG. 4B appears in the sensor information. The first candidate determination unit 4 calculates a distance between the distributions, i.e., between the face position distribution A stored as the normal range in the learning database 1 and the face position distribution C, and determines that the sensor information acquired by the acquisition unit 3 is not in the normal range when the distribution C is deviated from the distribution A and the deviation therefrom is equal to or larger than the first set value.

The sensor information acquired by the acquisition unit 3 is not limited to that indicating the position of the driver's face, and may be that further indicating an eye opening degree of the driver, speed and direction of movement of the driver's face, an orientation of the driver's face, a facial expression of the driver, and the like. In that case, the first candidate determination unit 4 preferably calculates the distance between the distributions in a vector space in a multidimensional space using, as feature quantities, the position of the driver's face, the eye opening degree of the driver, the speed and direction of movement of the driver's face, the orientation of the driver's face, the facial expression of the driver, and the like, and performs determination.

If it is determined by the first candidate determination unit 4 that the sensor information is not in the normal range (Step ST2; NO), the second candidate determination unit 5 determines whether there is a combination corresponding to the combination of the sensor information and the device information acquired by the acquisition unit 3, among the combinations of the sensor information and the device information stored in the learning database 1 (Step ST3). The second candidate determination unit 5 outputs a result of the determination to the determination unit 7. The details of the process of Step ST3 will be described in the "abnormality detection phase" described later, and the description will be continued here, assuming that the second candidate determination unit 5 determines that there is no corresponding combination (Step ST3; NO).

If it is determined by the second candidate determination unit 5 that there is no corresponding combination (Step ST3; NO), the reset determination unit 6 determines whether there is sensor information or device information corresponding to the sensor information or the device information acquired by the acquisition unit 3, in the sensor information or the device information stored in the behavior pattern database 2 (Step ST4). The reset determination unit 6 may determine that there is corresponding sensor information or device information when the sensor information or the device information acquired by the acquisition unit 3 is corresponding to any one of pieces of the sensor information or the device information stored in the behavior pattern database 2, or is corresponding to a plurality of pieces of the sensor information or the device information stored in the behavior pattern database 2. The reset determination unit 6 outputs a result of the determination to the determination unit 7.

If it is determined by the reset determination unit 6 that there is corresponding sensor information or device information (Step ST4; YES), the determination unit 7 determines that it is the normal state (Step ST5). In that case, the determination unit 7 instructs the update unit 8 to perform a registration process in the learning database 1.

Figure 5C:
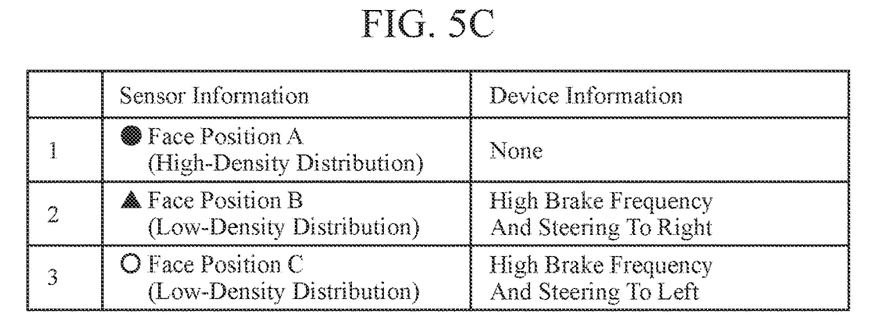

In response to the instruction from the determination unit 7, the update unit 8 registers the combination of the sensor information and the device information acquired by the acquisition unit 3 in the learning database 1 (Step ST6). Accordingly, the sensor information indicating the face position distribution C illustrated in FIG. 4B is newly registered, in the learning database 1, in combination with the device information acquired by the acquisition unit 3 together with the sensor information. For example, if the sensor information indicating the face position distribution C is acquired by the acquisition unit 3 together with device information indicating high brake frequency and steering to the left, both pieces of information are linked as illustrated in FIG. 5C and registered in the learning database 1.

When the update unit 8 receives the sensor information and the device information from the acquisition unit 3, the update unit 8 does not register in the learning database 1 but temporarily retains, that is, caches both pieces of information during the determination processes performed by the first candidate determination unit 4 and the second candidate determination unit 5.

Thereafter, if the reset determination unit 6 determines that there is corresponding sensor information or device information (Step ST4; YES), the update unit 8 registers the temporarily retained sensor information and device information in the learning database 1 as the combination of the sensor information and the device information in the normal state.

In addition, device information obtained as a result of the driver's performance of a type of behavior that is not stored in the behavior pattern database 2 may be registered as device information in the learning database 1.

Figure 6:
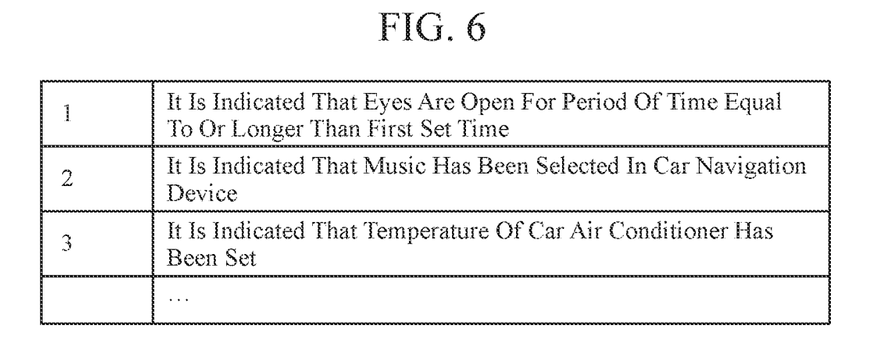
FIG. 6 is a table illustrating examples of conditions in relation to a behavior pattern database.

For example, it is assumed that information that satisfies the conditions illustrated in FIG. 6 is stored as the sensor information or the device information in the normal state in the behavior pattern database 2. More specifically, in the example of FIG. 6, the sensor information or the device information that corresponds to a right turn or left turn is not stored in the behavior pattern database 2. For this reason, regarding the driver's poor posture at the time of a right turn or left turn, on the basis of the fact that sensor information is obtained which satisfies any of the conditions in FIG. 6, for example, "It is indicated that eyes are open for a period of time equal to or longer than a first set time", the reset determination unit 6 determines that "Step ST4; YES" in the process of Step ST4.

Then, in the process of Step ST6 performed by the update unit 8, although device information related to the brake frequency and steering operation directions is not stored in the behavior pattern database 2 as illustrated in FIG. 6, device information indicating the brake frequency and the steering operation direction is newly registered in the learning database 1. The device information registered as described above can be said to be a behavior pattern in the normal state automatically collected by the abnormality detection device 10.

In addition, for example, when the device information acquired by the acquisition unit 3 indicates that the engine is stopped, the update unit 8 deletes the learning database 1 partially or entirely. Accordingly, the abnormality detection device 10 can cope with a case where the driver is changed to another person.

The update unit 8 may perform a deletion process of the learning database 1 at various timings besides the engine stop. For example, when the position of the driver's seat moves due to reclining adjustment of the driver's seat or the like, the update unit 8 may delete the learning database 1 entirely. The update unit 8 may delete information which has been registered in the learning database 1 for a period of time equal to or longer than a second set time. The update unit 8 may delete the learning database 1 when the sensor information acquired by the acquisition unit 3 indicates a change of the driver. The change of the driver can be determined using sensor information indicating a result of face authentication by the sensor 11, for example.

If it is determined by the reset determination unit 6 that there is no corresponding sensor information or device information (Step ST4; NO), the determination unit 7 determines that it is the abnormal state (Step ST7). In that case, the registration process in the learning database 1 is not performed. When the determination unit 7 determines that it is the abnormal state, an alarm may be output, or the vehicle may be controlled by automatic driving.

The "normal state data collection phase" has been described above. As described above, the abnormality detection device 10 learns the driver's habit, changes in the seat position, and the like, and updates the learning database 1 sequentially.

Figure 7A:
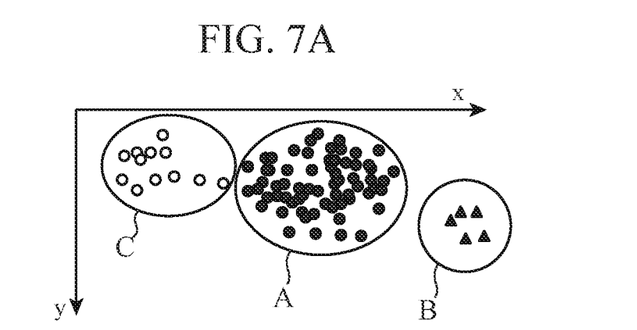
FIG. 7A is a diagram illustrating the positions of the driver's face in the learning database illustrated in FIG. 5C.

Next, the "abnormality detection phase" will be described. Hereinafter, as an example, a case will be described where the learning database 1 is that illustrated in FIG. 5C. FIG. 7A illustrates the face distributions A, B, and C in FIG. 5C.

After Step ST1, if the first candidate determination unit 4 determines that the sensor information acquired by the acquisition unit 3 is in the normal range (Step ST2; YES), the determination unit 7 determines that it is the normal state (Step ST8).

Figure 7B:
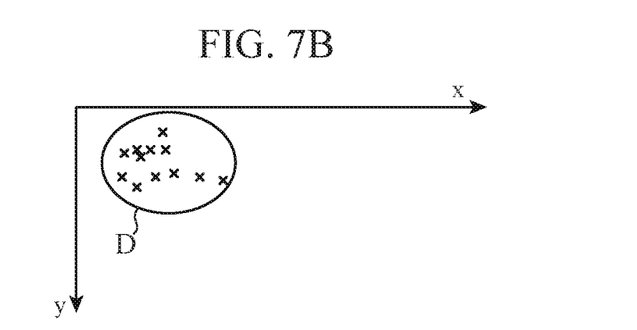
FIG. 7B is a diagram illustrating an example of a position of the face of the driver who has leaned forward and collapsed.

On the other hand, for example, it is assumed that the driver is brought into an abnormal state due to loss of consciousness or the like, cannot operate the brake or the steering wheel, and leans forward and collapses in the driver's seat, and thereby the position of the driver's face is moved to the position illustrated in a distribution D of FIG. 7B. In that case, sensor information indicating that the position of the face is D and device information indicating no brake operation and no steering operation are acquired in Step ST1. Then, in Step ST2 subsequent thereto, the process described in the "normal state data collection phase" is performed, and the first candidate determination unit 4 determines that the sensor information is not in the normal range. In that case (Step ST2; NO), the second candidate determination unit 5 determines whether there is a combination corresponding to the combination of the sensor information and the device information acquired by the acquisition unit 3, among the combinations of the sensor information and the device information stored in the learning database 1 (Step ST3).

First, the second candidate determination unit 5 extracts, from the learning database 1, a combination in which the sensor information is corresponding to the sensor information acquired by the acquisition unit 3. More specifically, the second candidate determination unit 5 extracts, from the learning database 1, a combination in which the distribution indicates closeness to the face position distribution D, the closeness being equal to or larger than a second set value. As illustrated in FIGS. 7A and 7B, the distribution D is regarded as corresponding to the distribution C, and thus a combination of the distribution C and high brake frequency and steering to the left is extracted, the combination being illustrated in FIG. 5C. In some cases, not one combination but multiple combinations may be extracted.

Subsequently, the second candidate determination unit 5 determines whether the device information acquired by the acquisition unit 3 is corresponding to the device information of the combination extracted from the learning database 1. Since the device information acquired by the acquisition unit 3 indicates "no brake operation and no steering operation" and the extracted device information indicates "high brake frequency and steering to the left", the pieces of the device information are determined not to be corresponding to each other. In that case, the second candidate determination unit 5 determines that there is no combination corresponding to the combination of the sensor information and the device information acquired by the acquisition unit 3 among the combinations of the sensor information and the device information stored in the learning database 1.

The process performed if it is determined by the second candidate determination unit 5 that there is no corresponding combination (Step ST3; NO) is as described in the "normal state data collection phase" above.

On the other hand, if it is determined by the second candidate determination unit 5 that there is a corresponding combination (Step ST3; YES), the determination unit 7 determines that it is the normal state (Step ST8).

Sensor information or device information in the abnormal state, in addition to that in the normal state, may be stored in the behavior pattern database 2. In that case, in Step ST3, when referring to the behavior pattern database 2 to find that it is clearly the abnormal state, the second candidate determination unit 5 may instruct, without referring to the learning database 1, the determination unit 7 to determine the abnormal state.

As the sensor information or the device information in the abnormal state, for example, information that satisfies one of the following conditions is stored in the behavior pattern database 2.

It is indicated that the driver's eyes or face has not been detected for a period of time equal to or longer than a third set time.

It is indicated that no action has been taken to stop an alarm.

It is indicated that the vehicle speed is 30 km/h or higher and there is no brake operation.

An abnormal heart rate is indicated.

The second candidate determination unit 5 instructs the determination unit 7 to determine the abnormal state when the sensor information or the device information acquired by the acquisition unit 3 is corresponding to one or more pieces of the sensor information or the device information in the abnormal state stored in the behavior pattern database 2.

The second candidate determination unit 5 may perform the determination in Step ST3 by extracting, from the learning database 1, a combination in which the device information is corresponding to the device information acquired by the acquisition unit 3, and then determining whether the sensor information acquired by the acquisition unit 3 is corresponding to the sensor information of the combination extracted from the learning database 1.

As described above, the abnormality detection device 10 sequentially learns the combinations of the sensor information and the device information in the normal state to register the combinations in the learning database 1, and uses the combinations for discriminating the abnormal state. By learning and using the combinations of the sensor information and the device information in the normal state, the abnormality detection device 10 can accurately discriminate two cases that are confusing in terms of postures, i.e., a case where the driver is leaning forward and peering through the windshield or resting his/her chin on his/her hand while driving, and a case where the driver collapses due to loss of consciousness or the like. Therefore, the abnormality detection device 10 improves the discrimination accuracy between abnormal and normal states as compared with the case where the posture in the normal state is learned and used for the discrimination of the abnormal state as in Patent Literature 1 above.

Although the abnormality detection device 10 is mounted on the vehicle in the above description, the abnormality detection device 10 may be built in a server that is communicable with the sensor 11 and the vehicle device 12 and is placed outside the vehicle.

Alternatively, the abnormality detection device 10 may be built in a mobile terminal such as a smartphone or a tablet terminal that is communicable with the sensor 11 and the vehicle device 12 and is brought into the vehicle. In that case, a camera provided in the mobile terminal may be used as the camera of the sensor 11.

In the above description, the abnormality detection device 10 has been described as a device that is mounted on a vehicle and detects an abnormal state of a driver of the vehicle. However, the abnormality detection device 10 may be used for other purposes. The abnormality detection device 10 may be a device that detects that an abnormal state has occurred in a house, for example, by using a monitoring camera or a sensor installed in the house, or a camera provided in a home appliance such as an air conditioner or a refrigerator as the sensor 11, and acquiring the device information from each home appliance.

For example, the update unit 8 sequentially registers, in the learning database 1, combinations of the sensor information and the device information in the normal state such as "when a person is at a position E in the living room, the person is watching TV". When the first candidate determination unit 4 determines after such registration that there is a person at the position E that is out of the normal range of the sensor information, the second candidate determination unit 5 extracts the combination of "when a person is at a position E in the living room, the person is watching TV" from the learning database 1; however, when the device information acquired at that time by the acquisition unit 3 indicates that the TV is powered off, and in addition, the reset determination unit 6 determines that there is no corresponding information, it is detected that a resident is in the abnormal state, for example, the resident has collapsed and cannot move. As for the behavior pattern database 2 in that case, information indicating that the resident is in the normal state, for example, sensor information that satisfies the condition of "It is indicated that eyes are open for a period of time equal to or longer than a first set time" may be possibly stored.

For another example, when the first candidate determination unit 4 determines that there is a person at the position E that is out of the normal range of the sensor information, the second candidate determination unit 5 extracts the combination of "when a person is at a position E in the living room, the person is watching TV" from the learning database 1; however, when the device information acquired at that time by the acquisition unit 3 indicates that the TV is powered off, and in addition, the reset determination unit 6 determines that there is no corresponding information, it is detected that a suspicious person has broken into the house. As for the behavior pattern database 2 in that case, information indicating that there is no suspicious person and the house is in the normal state, for example, sensor information that satisfies the condition of "It is indicated that persons have had a conversation with smiles" may be possibly stored.

As described above, the abnormality detection device 10 of the first embodiment sequentially learns the combinations of the sensor information and the device information in the normal state, registers the combinations in the learning database 1, and uses the combinations to discriminate the abnormal state. Thereby, it is possible to accurately discriminate between normal and abnormal states that are confusing due to similar postures, such as a case where the driver is leaning forward and peering through the windshield or resting his/her chin on his/her hand while driving, and a case where the driver collapses due to loss of consciousness or the like. Therefore, the discrimination accuracy between abnormal and normal states is improved.

The abnormality detection device 10 sequentially updates the learning database Thereby, the abnormality detection device 10 can detect the occurrence of an abnormal state while adapting, in a state of suppressing overfitting, to a habit of a person to be detected, for example, when the person is a driver, a habit thereof and changes in a seat position.

Because the behavior pattern database 2 is created in advance manually rather than automatically, it is difficult to cover all the behavior patterns that are generally considered to be those in the normal state. However, the abnormality detection device 10 can perform a process as if the abnormality detection device 10 supplemented the behavior pattern database 2, by automatically registering, in the learning database 1, device information corresponding to a behavior pattern in the normal state.

The second candidate determination unit 5 extracts, from the learning database 1, one or more combinations in each of which the sensor information is corresponding to the acquired sensor information, and when there is no device information corresponding to the acquired device information in the device information of the extracted combinations, the second candidate determination unit 5 determines that there is no combination corresponding to the combination of the acquired sensor information and the acquired device information in the learning database 1. Consequently, the second candidate determination unit 5 can appropriately determine whether there is a corresponding combination in the learning database 1.

The update unit 8 temporarily retains the acquired sensor information and device information, and in a case where it is determined by the first candidate determination unit 4 that the sensor information is not in the normal range, when it is determined by the second candidate determination unit 5 that there is no corresponding combination and it is determined by the reset determination unit 6 that there is corresponding sensor information or device information, the update unit 8 registers a combination of the temporarily retained sensor information and device information in the learning database 1. Consequently, the update unit 8 can perform registration in the learning database 1 at an appropriate timing while effectively using a storage region of the abnormality detection device 10.

The acquisition unit 3 acquires sensor information indicating the state of the driver of the vehicle. Consequently, the abnormality detection device 10 can be used as a device that detects whether the driver of the vehicle is in the abnormal state such as loss of consciousness.

In the present invention, any component of the embodiment can be modified, or any component of the embodiment can be omitted, within the scope of the invention.

INDUSTRIAL APPLICABILITY

As described above, the abnormality detection device according to the present invention can improve the discrimination accuracy between abnormal and normal states, and is therefore suitably used as a device that detects an abnormal state of a driver of a vehicle, for example.

REFERENCE SIGNS LIST

1: Learning database, 2: Behavior pattern database, 3: Acquisition unit, 4: First candidate determination unit, 5: Second candidate determination unit, 6: Reset determination unit, 7: Determination unit, 8: Update unit, 10: Abnormality detection device, 11: Sensor, 12: Vehicle device, 101: Processing circuit, 102: Memory, 103: CPU, 104: HDD, 105: Input interface device, 106: Output interface device.

The invention claimed is:

1. An abnormality detection device comprising:
processing circuitry
to acquire sensor information indicating a state of a person and device information indicating a state of a device;
to determine whether the acquired sensor information is in a normal range;
to determine whether there is a combination corresponding to a combination of the acquired sensor information and the acquired device information in a learning database in which one or more combinations of the sensor information and the device information in a normal state are stored;
to determine whether there is sensor information or device information corresponding to the acquired sensor information or the acquired device information in a behavior pattern database in which the sensor information or the device information in the normal state is stored;
in a case where it is determined that the acquired sensor information is not in the normal range,
to determine that a current state is in the normal state when it is determined that there is the corresponding combination, and to determine that the current state is in an abnormal state when it is determined that there is no corresponding combination and no corresponding sensor information or device information; and
in the case where it is determined that the acquired sensor information is not in the normal range,
to register the combination of the acquired sensor information and the acquired device information in the learning database when it is determined that there is no corresponding combination, and it is determined that there is the corresponding sensor information or device information.

2. The abnormality detection device according to claim 1, wherein the processing circuitry extracts, from the learning database, one or more combinations in each of which the sensor information is corresponding to the acquired sensor information, and when there is no device information corresponding to the acquired device information in the device information of the extracted combinations, the processing circuitry determines that there is no combination corresponding to the combination of the acquired sensor information and the acquired device information in the learning database.

3. The abnormality detection device according to claim 1, wherein the processing circuitry temporarily retains the acquired sensor information and the acquired device information, and in the case where it is determined that the acquired sensor information is not in the normal range, when it is determined that there is no corresponding combination and it is determined that there is the corresponding sensor information or device information, the processing circuitry registers a combination of the temporarily retained sensor information and the temporarily retained device information in the learning database.

4. The abnormality detection device according to claim 1, wherein the processing circuitry acquires the sensor information indicating a state of a driver of a vehicle.

5. An abnormality detection method comprising:
acquiring sensor information indicating a state of a person and device information indicating a state of a device;
determining whether the acquired sensor information is in a normal range;
determining whether there is a combination corresponding to a combination of the acquired sensor information and the acquired device information in a learning database in which one or more combinations of the sensor information and the device information in a normal state are stored;

determining whether there is sensor information or device information corresponding to the acquired sensor information or the acquired device information in a behavior pattern database in which the sensor information or the device information in the normal state is stored;

in a case where it is determined that the acquired sensor information is not in the normal range, determining that a current state is in the normal state when it is determined that there is the corresponding combination, and determining that the current state is in an abnormal state when it is determined that there is no corresponding combination and no corresponding sensor information or device information; and in the case where it is determined that the acquired sensor information is not in the normal range, registering the combination of the acquired sensor information and the acquired device information in the learning database when it is determined that there is no corresponding combination, and it is determined that there is the corresponding sensor information or device information.

* * * * *